(12) United States Patent
Kong et al.

(10) Patent No.: US 9,393,544 B2
(45) Date of Patent: Jul. 19, 2016

(54) METHOD OF PREPARING ESTER COMPOUND AND ESTER COMPOUND PREPARED THEREBY

(71) Applicant: LG CHEM, LTD., Seoul (KR)

(72) Inventors: Myungjin Kong, Daejeon (KR); Won Jae Lee, Daejeon (KR); Yong-Jin Choe, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/556,688

(22) Filed: Dec. 1, 2014

(65) Prior Publication Data
US 2015/0152036 A1 Jun. 4, 2015

(30) Foreign Application Priority Data

Dec. 3, 2013 (KR) .................. 10-2013-0149300
Nov. 12, 2014 (KR) .................. 10-2014-0157086

(51) Int. Cl.
| C07C 67/02 | (2006.01) |
| B01J 19/10 | (2006.01) |
| C07D 317/24 | (2006.01) |
| C07D 319/06 | (2006.01) |

(52) U.S. Cl.
CPC ............... *B01J 19/10* (2013.01); *C07D 317/24* (2013.01); *C07D 319/06* (2013.01)

(58) Field of Classification Search
CPC ...................................... C07C 67/02
See application file for complete search history.

(56) References Cited

U.S. PATENT DOCUMENTS

| 2003/0167681 A1 | 9/2003 | Delgado Puche |
| 2011/0192072 A1 | 8/2011 | Steele et al. |

FOREIGN PATENT DOCUMENTS

| JP | 06111366 A * | 4/1994 |
| JP | 2001-261672 | 9/2001 |
| JP | 2007-543665 A | 11/2007 |
| WO | WO 2008084227 A1 * | 7/2008 |

OTHER PUBLICATIONS

Wang, Y., et al. "Selective Esterifications of Primary Alcohols in a Water-Containing Solvent." Organic Letters. (2012), vol. 14, No. 18, pp. 4910-4913.*
Yong Wang et al., "Selective Esterifications of Primary Alcohols in a Water-Containing Solvent," Organic Letters, 2012, 14 (18), pp. 4910-4913.
Carolina X.A. da Silva et al., "The influence of impurities on the acid-catalyzed reaction of glycerol with acetone," Biomass and Bioenergy 35, 2011, pp. 3547-3551.
Sandra Y. Giraldo et al., "Comparison of glycerol ketals, glycerol acetates and branched alcohol-derived fatty esters as cold-flow improvers for palm biodiesel," Fuel 108, 2013, pp. 709-714.
Eva Garcia et al., "New Class of Acetal Derived from Glycerin as a Biodiesel Fuel Component," Energy & Fuels, vol. 22, No. 6, 2008, pp. 4274-4280.
J. Deutsch et al., "Investigations on heterogeneously catalysed condensations of glycerol to cyclic acetals," Journal of Catalysis 245, 2007, pp. 428-435.
Claudio J. A. Mota et al., "Glycerin Derivatives as Fuel Additives: the Addition of Glycerol/Acetone Ketal (Solketal) in Gasolines," Energy Fuels, 24, 2010, pp. 2733-2736.

* cited by examiner

*Primary Examiner* — Noble Jarrell
*Assistant Examiner* — John S Kenyon
(74) *Attorney, Agent, or Firm* — Dentons US LLP

(57) ABSTRACT

This invention relates to a method of preparing an ester compound, including adding carboxylic acid to a mixture of glycerol and acetone in the presence of a sulfuric acid catalyst and applying an ultrasonic wave to induce an esterification reaction, and to an ester compound prepared thereby.

10 Claims, No Drawings

US 9,393,544 B2

METHOD OF PREPARING ESTER COMPOUND AND ESTER COMPOUND PREPARED THEREBY

CROSS REFERENCE TO RELATED APPLICATIONS

This application claims the benefit of Korean Patent Application Nos. KR 10-2013-0149300, filed Dec. 3, 2013 and KR 10-2014-0157086, filed Nov. 12, 2014, which are hereby incorporated by reference in their entirety into this application.

BACKGROUND OF THE INVENTION

1. Technical Field

The present invention relates to a method of preparing an ester compound, and more particularly, to a method of preparing an ester compound, which may increase the reaction yield using sonication and enables the preparation process to be simplified.

2. Description of the Related Art

Ester refers to a compound produced by a condensation reaction between an alcohol and an acid while eliminating water, and mainly indicates carboxylic acid ester.

Conventional preparation of such an ester compound includes synthesis of an ester compound via a two-step esterification comprising adding acetone and sulfuric acid to glycerol to give a product and reacting the product with formic acid, as disclosed in Yong Wang, Bilal A. Aleiwi, Qinghui Wang and Michio Kurosu. Selective esterifications of primary alcohols in a water-containing solvent. Org. Lett., 2012, 14 (18), pp 4910-4913.

However, the conventional method is problematic because the esterification reaction is not high in yield and is carried out via two steps, thus requiring additional process equipment and increasing the synthesis time of the ester compound, undesirably resulting in low profitability.

Accordingly, there is a need for research into novel ester compound synthesis methods able to directly synthesize an ester compound from glycerol by increasing the yield of esterification reaction and simplifying the preparation process.

CITATION LIST

Patent Literature (Non-Patent Document 1) Yong Wang, Bilal A. Aleiwi, Qinghui Wang and Michio Kurosu. Selective esterifications of primary alcohols in a water-containing solvent. Org. Lett., 2012, 14 (18), pp 4910-4913.

SUMMARY OF THE INVENTION

Therefore, the present invention has been made keeping in mind the above problems occurring in the related art, and an object of the present invention is to provide a novel method of preparing an ester compound, which may increase the yield of esterification reaction and enables an ester compound to be directly synthesized from glycerol under specific synthesis conditions, without the need for many reaction steps.

In order to accomplish the above object, the present invention provides a method of preparing an ester compound, comprising adding carboxylic acid to a mixture of glycerol and acetone in the presence of a sulfuric acid catalyst and applying an ultrasonic wave to induce an esterification reaction.

In addition, the present invention provides an ester compound, prepared by the method as above.

According to the present invention, a method of preparing an ester compound can increase the yield of esterification reaction and can directly synthesize an ester compound from glycerol under specific synthesis conditions without the need for many reaction steps.

DESCRIPTION OF THE PREFERRED EMBODIMENTS

Hereinafter, a detailed description will be given of a method of preparing an ester compound and an ester compound prepared thereby according to the present invention.

The present invention is intended to increase the yield of esterification reaction by applying an ultrasonic wave upon esterification reaction, and also to simplify the preparation process so that an ester compound may be directly synthesized from glycerol. Thus, the process of preparing the ester compound may increase the reaction yield and may be simple compared to conventional processes, thus drastically shortening the reaction time and also remarkably decreasing the preparation cost.

To this end, a method of preparing an ester compound according to the present invention includes adding carboxylic acid to a mixture of glycerol and acetone in the presence of a sulfuric acid catalyst and applying an ultrasonic wave to thus induce an esterification reaction.

In the method of preparing the ester compound according to the present invention, the glycerol may include any commercially available glycerol without particular limitation so long as it is useful for esterification reaction. The use of glycerol having a purity of 60~99.5% is preferable.

In the method of preparing the ester compound according to the present invention, the acetone may include any commercially available acetone without particular limitation so long as it is useful for glycerol reaction. The use of acetone having a purity of 40~99.5% is preferable. In the present invention, acetone may be added in an amount of 3~15 equivalents based on the alcohol. If the amount of acetone is less than 3 equivalents, the conversion of alcohol and the selectivity of esterification reaction may decrease. In contrast, if the amount of acetone exceeds 15 equivalents, there is no improvement in special effects due to the addition thereof.

In the method of preparing the ester compound according to the present invention, the carboxylic acid may be used without particular limitation so long as it has a COOH group. Preferably useful is formic acid. In the present invention, carboxylic acid may be added in an amount of 1~5 equivalents based on the glycerol. If the amount of carboxylic acid is less than 1 equivalent, the conversion of glycerol and the selectivity of ester compound may decrease. In contrast, if the amount thereof exceeds 5 equivalents, there is no improvement in special effects due to the addition thereof.

As used herein, the equivalent has the same concept as the mole because glycerol and formic acid react at 1:1.

In the method of preparing the ester compound according to the present invention, the intensity of the ultrasonic wave may be appropriately adjusted depending on the need of a user. Preferably, an ultrasonic wave is applied at a power density of 20~700 $W/cm^2$, and more preferably 70~500 $W/cm^2$. If the power density of the ultrasonic wave is less than 20 $W/cm^2$, the reaction may not occur, undesirably lowering the reaction efficiency. In contrast, if the power density of the ultrasonic wave exceeds 700 $W/cm^2$, the reaction solution may be unfavorably overheated. Furthermore, the ultrasonic reaction time may be appropriately adjusted depending on the need of a user. Preferably, the ultrasonic wave is applied for 1~400 min, and more preferably for 5~100 min.

In the method of preparing the ester compound according to the present invention, the esterification reaction after addition of formic acid to glycerol and acetone may be carried out at a temperature ranging from −20 to 10° C. When the reaction temperature falls in the range of −20 to 10° C., optimal reactivity may result. If the reaction temperature falls outside of the above range, reactivity may drastically decrease.

The method of preparing the ester compound according to the present invention may be performed in the following two manners.

In the first manner as shown in Scheme 1 below, the preparation method includes adding acetone and sulfuric acid to glycerol (Step 1); and adding the reaction product of Step 1 with carboxylic acid (e.g. formic acid) and then applying an ultrasonic wave, thus preparing an ester compound (Step 2).

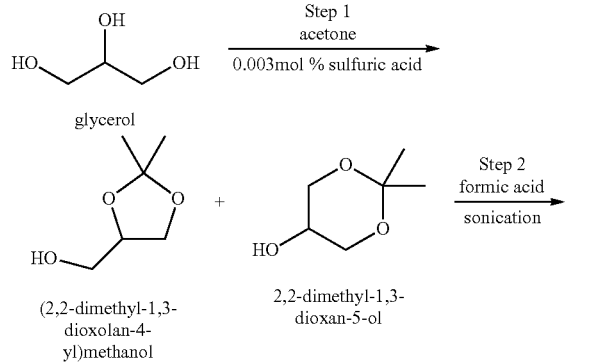

[Scheme 1]

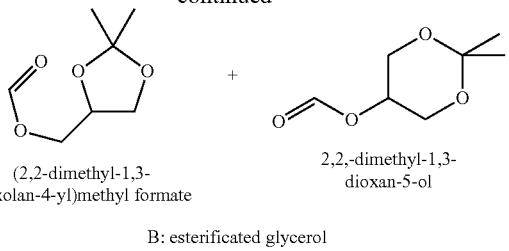

In the second manner as shown in Scheme 2 below, the preparation method includes adding formic acid to a mixture of glycerol and acetone in the presence of a sulfuric acid catalyst, and simultaneously applying an ultrasonic wave to induce an esterification reaction, thereby preparing an ester compound through a one-pot process.

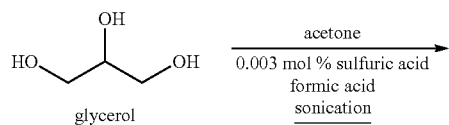

[Scheme 2]

The present invention addresses an ester compound prepared by the method as above.

The ester compound prepared by the method according to the present invention, especially the method as shown in Scheme 1 or 2, may include (2,2-dimethyl-1,3-dioxolan-4-yl)methyl formate, 2,2-dimethyl-1,3-dioxan-5-yl formate, glyceryl formate or 2-hydroxypropane-1,3-diyl diformate.

The ester compound prepared by the method as above has a yield of 30% or more. Furthermore, since the total reaction time is quite short compared to when using conventional techniques, high profitability may result.

A better understanding of the present invention may be obtained via the following examples that are set forth to illustrate, but are not to be construed as limiting the present invention.

EXAMPLES

Preparation of Ester Compound

Example 1

9.21 g (0.10 mol) of glycerol, 29.0 g (0.50 mol, 5 eq) of acetone, and 0.020 g (0.0003 mol, 0.003 eq) of sulfuric acid (pKa: −3.0) were added, and stirred at 25° C. for 15 hr, thus preparing a solketal solution.

Then, 27.00 g of the prepared solketal solution (including a 0.07 mol alcohol solution obtained by mixing (2,2-dimethyl-1,3-dioxolan-4-yl)methanol and 2,2-dimethyl-1,3-dioxan-5-ol at 99:1 and the remainder of acetone), and 3.25 g (0.07 mol, 1 eq) of formic acid were placed in a flask reactor, and a circulator (Julabo F32) was set to a reaction temperature of 0° C., after which sonication was conducted at a power density of 460 W/cm$^2$ for 30 min using an ultrasonic processor (Hielscher Ultrasonics GmbH., Model: UP400S), thus preparing an ester compound. As such, the sonotrode of the ultrasonic processor was a tip type.

Example 2

An ester compound was prepared in the same manner as in Example 1, with the exception that 4.875 g (0.105 mol, 1.5 eq) of formic acid was used.

Example 3

An ester compound was prepared in the same manner as in Example 1, with the exception that 6.5 g (0.14 mol, 2 eq) of formic acid was used.

Example 4

An ester compound was prepared in the same manner as in Example 1, with the exception that 9.75 g (0.21 mol, 3 eq) of formic acid was used.

Example 5

An ester compound was prepared in the same manner as in Example 1, with the exception that 13 g (0.28 mol, 4 eq) of formic acid was used.

Example 6

An ester compound was prepared in the same manner as in Example 5, with the exception that the maximum amplitude of the ultrasonic processor was set to 210 μm depending on the sonotrode of the ultrasonic processor.

Example 7

9.21 g (0.10 mol) of glycerol, 29.0 g (0.50 mol, 5 eq) of acetone, 0.020 g (0.0003 mol, 0.003 eq) of sulfuric acid (pKa: −3.0) and 13 g (0.28 mol, 4 eq) of formic acid were placed in a flask reactor, a circulator (Julabo F32) was set to a reaction temperature of 0° C., and sonication was carried out at a power density of 460 W/cm$^2$ for 6 min using an ultrasonic processor (Hielscher Ultrasonics GmbH., Model: UP400S), thus preparing an ester compound. The maximum amplitude of the ultrasonic processor was 210 μm.

Comparative Example 1

An ester compound was prepared in the same manner as in Example 1, with the exception that 9.75 g (0.21 mol, 3 eq) of formic acid was used, and the reaction was carried out under reflux at 70° C. for 1 hr, instead of the ultrasonic reaction.

Comparative Example 2

An ester compound was prepared in the same manner as in Example 7, with the exception that the same equivalent of hydrochloric acid instead of sulfuric acid was used.

Comparative Example 3

An ester compound was prepared in the same manner as in Example 7, with the exception that the same equivalent of nitric acid instead of sulfuric acid was used.

The reaction conditions of Examples 1 to 7 and Comparative Examples 1 to 3 are shown in Table 1 below.

TABLE 1

|  | Formic acid (eq) | Reaction Temp. (° C.) | Sonotrode Maximum amplitude (μm) | Reaction time (Step 1/Step 2) (hr) |
| --- | --- | --- | --- | --- |
| Ex. 1 | 1.0 | 0 | 100 | 15/0.5 |
| Ex. 2 | 1.5 | 0 | 100 | 15/0.5 |
| Ex. 3 | 2.0 | 0 | 100 | 15/0.5 |
| Ex. 4 | 3.0 | 0 | 100 | 15/0.5 |
| Ex. 5 | 4.0 | 0 | 100 | 15/0.5 |
| Ex. 6 | 4.0 | 0 | 210 | 15/0.5 |
| Ex. 7 | 4.0 | 0 | 210 | 0.1 |
| C. Ex. 1 | 3.0 | 70 | — | 15/1.0 |
| C. Ex. 2 | 1.0 | 0 | 210 | 0.1 |
| C. Ex. 3 | 1.0 | 0 | 210 | 0.1 |

Test Example

For the ester compounds of the above examples and comparative examples, unreacted glycerol and ester compounds were analyzed using gas chromatography (GC 6890N, Agilent) based on GC area % analysis. The glycerol conversion, esterification selectivity, and esterification yield were calculated by Equations 1 to 3 below. The results are shown in Table 2 below.

$$\text{Glycerol conversion (\%)} = 100 - \text{glycerol GC area \% after reaction} \quad \text{[Equation 1]}$$

$$\text{Esterification selectivity (\%)} = 100 \times (\text{produced ester compound GC area \%})/(\text{alcohol conversion}) \quad \text{[Equation 2]}$$

$$\text{Esterification yield (\%)} = (\text{glycerol conversion} \times \text{esterification selectivity})/(100) \quad \text{[Equation 3]}$$

TABLE 2

|  | Glycerol conversion (%) | Esterification selectivity (%) | Esterification yield (%) | Reaction time (Step 1/Step 2) (hr) |
| --- | --- | --- | --- | --- |
| Ex. 1 | 32.3 | 79.6 | 25.7 | 15/0.5 |
| Ex. 2 | 41.2 | 82.8 | 34.1 | 15/0.5 |
| Ex. 3 | 55.8 | 75.2 | 42.0 | 15/0.5 |
| Ex. 4 | 46.8 | 89.3 | 41.8 | 15/0.5 |
| Ex. 5 | 50.5 | 90.9 | 45.9 | 15/0.5 |
| Ex. 6 | 61.9 | 89.2 | 55.2 | 15/0.5 |
| Ex. 7 | 97.3 | 34.1 | 33.2 | 0.1 |
| C. Ex. 1 | 75.2 | 40.0 | 30.1 | 15/1.0 |
| C. Ex. 2 | 5.1 | 57.0 | 4.1 | 0.5 |
| C. Ex. 3 | 6.4 | 43.8 | 2.8 | 0.5 |

As is apparent from Table 2, Examples 1 to 7 using the method of preparing the ester compound according to the present invention exhibited a stable yield at a predetermined level or more. Particularly in Example 4 and Comparative Example 1 using the same equivalent of formic acid, the reaction temperature was lowered but the reaction yield was higher by at least 10% in Example 4 than in Comparative Example 1.

In Example 7 using the one-pot reaction according to the present invention, the yield was 33.2%, which is similar to when using the conventional method, but the reaction time was 6 min, which is equal to or less than 1/150 of the conventional reaction time of 15 hr or longer. Also, in Comparative Examples 2 and 3 using hydrochloric acid or nitric acid in lieu of sulfuric acid, the glycerol conversion was too low, and thus the total yield was also low. Hence, the method of preparing the ester compound according to embodiments of the present invention can increase the reaction yield of the ester compound and also can drastically reduce the preparation time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of preparing an ester compound, comprising:
    adding carboxylic acid to a mixture of glycerol and acetone in the presence of a sulfuric acid catalyst, and
    applying an ultrasonic wave to induce an esterification reaction,
    wherein the ester compound is any one or more selected from the group consisting of (2,2-dimethyl-1,3-dioxolan-4-yl)methyl formate, 2,2-dimethyl-1,3-dioxan-5-yl formate, glyceryl formate and 2-hydroxypropane-1,3-diyl diformate.
2. The method of claim 1, wherein the method is a one-pot process.

3. The method of claim 1, wherein applying the ultrasonic wave is performed at a power density of 20-700 W/cm$^2$.

4. The method of claim 1, wherein applying the ultrasonic wave is performed at a power density of 70-500 W/cm$^2$.

5. The method of claim 1, wherein applying the ultrasonic wave is performed for 1-400 min.

6. The method of claim 1, wherein applying the ultrasonic wave is performed for 5-100 min.

7. The method of claim 1, wherein the acetone is added in an amount of 3-15 equivalents based on the glycerol.

8. The method of claim 1, wherein the carboxylic acid is formic acid, which is added in an amount of 1-5 equivalents based on the glycerol.

9. The method of claim 1, wherein the esterification reaction is carried out at −20-10° C.

10. The method of claim 1, wherein the ester is prepared at a yield of 30% or more.

\* \* \* \* \*